United States Patent
Garrison et al.

(10) Patent No.: US 10,314,646 B2
(45) Date of Patent: Jun. 11, 2019

(54) APPARATUS FOR PERFORMING AN ELECTROSURGICAL PROCEDURE

(71) Applicant: COVIDIEN LP, Mansfield, MA (US)

(72) Inventors: David M. Garrison, Longmont, CO (US); Jeffrey M. Roy, Boulder, CO (US); Duane E. Kerr, Loveland, CO (US)

(73) Assignee: COVIDIEN LP, Mansfield, MA (US)

( * ) Notice: Subject to any disclaimer, the term of this patent is extended or adjusted under 35 U.S.C. 154(b) by 348 days.

(21) Appl. No.: 15/194,171

(22) Filed: Jun. 27, 2016

(65) Prior Publication Data

US 2016/0302851 A1    Oct. 20, 2016

Related U.S. Application Data

(60) Continuation of application No. 14/035,423, filed on Sep. 24, 2013, now Pat. No. 9,375,227, which is a (Continued)

(51) Int. Cl.
*A61B 17/29* (2006.01)
*A61B 18/14* (2006.01)
(Continued)

(52) U.S. Cl.
CPC ...... *A61B 18/1445* (2013.01); *A61B 17/2833* (2013.01); *A61B 17/29* (2013.01); *A61B 17/2909* (2013.01); *A61B 18/1206* (2013.01); *A61B 2017/2925* (2013.01); *A61B 2017/2932* (2013.01); *A61B 2017/2936* (2013.01);
(Continued)

(58) Field of Classification Search
CPC . A61B 17/2833; A61B 17/29; A61B 17/2909; A61B 18/1206; A61B 18/1445; A61B 2017/2925; A61B 2017/2932; A61B 2017/2936; A61B 2018/00589; A61B 2018/00595; A61B 2018/00601;
(Continued)

(56) References Cited

U.S. PATENT DOCUMENTS

D263,020 S    2/1982   Rau, III
D295,893 S    5/1988   Sharkany et al.
(Continued)

FOREIGN PATENT DOCUMENTS

DE    2415263 A1    10/1975
DE    2514501 A1    10/1976
(Continued)

OTHER PUBLICATIONS

US 5,273,887 A1, 08/2001, Yamauchi et al. (withdrawn)
(Continued)

*Primary Examiner* — Michael F Peffley

(57) ABSTRACT

A forceps includes a housing having a shaft. An end effector assembly operatively connects to a distal end of the shaft and includes a pair of first and second jaw members. One or both of the first and second jaw members is movable relative to the other jaw member from a clamping position to an open position. A resilient member operably couples to the first and second jaw members. The resilient member is configured to bias the first and second jaw members in the clamping position and provide a closure force on tissue disposed therebetween.

19 Claims, 6 Drawing Sheets

Related U.S. Application Data division of application No. 12/792,330, filed on Jun. 2, 2010, now Pat. No. 8,540,749.

(51) Int. Cl.
*A61B 17/28* (2006.01)
*A61B 18/12* (2006.01)
*A61B 18/00* (2006.01)
*A61B 90/00* (2016.01)

(52) U.S. Cl.
CPC ............. *A61B 2018/0063* (2013.01); *A61B 2018/00589* (2013.01); *A61B 2018/00595* (2013.01); *A61B 2018/00601* (2013.01); *A61B 2018/126* (2013.01); *A61B 2018/1253* (2013.01); *A61B 2090/034* (2016.02)

(58) Field of Classification Search
CPC .... A61B 2018/0063; A61B 2018/1253; A61B 2018/126; A61B 2090/034
See application file for complete search history.

(56) References Cited

U.S. PATENT DOCUMENTS

| | | | |
|---|---|---|---|
| D295,894 S | 5/1988 | Sharkany et al. | |
| 4,760,848 A * | 8/1988 | Hasson | A61B 17/062 294/115 |
| 5,250,056 A * | 10/1993 | Hasson | A61B 17/29 606/151 |
| 5,261,918 A | 11/1993 | Phillips et al. | |
| D348,930 S | 7/1994 | Olson | |
| 5,327,908 A * | 7/1994 | Gerry | G01B 3/38 600/587 |
| 5,411,519 A | 5/1995 | Tovey et al. | |
| 5,454,378 A | 10/1995 | Palmer et al. | |
| 5,527,313 A | 6/1996 | Scott et al. | |
| D384,413 S | 9/1997 | Zlock et al. | |
| 5,954,731 A | 9/1999 | Yoon | |
| D424,694 S | 5/2000 | Tetzlaff et al. | |
| D425,201 S | 5/2000 | Tetzlaff et al. | |
| D449,886 S | 10/2001 | Tetzlaff et al. | |
| D457,958 S | 5/2002 | Dycus et al. | |
| D457,959 S | 5/2002 | Tetzlaff et al. | |
| 6,726,686 B2 | 4/2004 | Buysse et al. | |
| D493,888 S | 8/2004 | Reschke | |
| D496,997 S | 10/2004 | Dycus et al. | |
| D499,181 S | 11/2004 | Dycus et al. | |
| D509,297 S | 9/2005 | Wells | |
| D525,361 S | 7/2006 | Hushka | |
| 7,083,618 B2 * | 8/2006 | Couture | A61B 18/1445 606/49 |
| 7,101,371 B2 | 9/2006 | Dycus et al. | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al. | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| 7,540,872 B2 | 6/2009 | Schechter et al. | |
| 7,766,910 B2 | 8/2010 | Hixson et al. | |
| 7,887,536 B2 | 2/2011 | Johnson et al. | |
| 7,918,848 B2 | 4/2011 | Lau et al. | |
| 7,951,150 B2 | 5/2011 | Johnson et al. | |
| 8,016,827 B2 | 9/2011 | Chojin | |
| 8,112,871 B2 | 2/2012 | Brandt et al. | |
| 8,114,122 B2 * | 2/2012 | Nau, Jr. | A61B 18/1445 606/207 |
| 8,133,254 B2 | 3/2012 | Dumbauld et al. | |
| 8,142,473 B2 | 3/2012 | Cunningham | |
| 8,162,965 B2 | 4/2012 | Reschke et al. | |
| 8,187,273 B2 | 5/2012 | Kerr et al. | |
| 8,197,479 B2 | 6/2012 | Olson et al. | |
| 8,226,650 B2 | 7/2012 | Kerr | |
| 8,251,994 B2 | 8/2012 | McKenna et al. | |
| 8,266,783 B2 | 9/2012 | Brandt et al. | |
| 8,277,446 B2 | 10/2012 | Heard | |
| 8,277,447 B2 | 10/2012 | Garrison et al. | |
| 8,282,634 B2 | 10/2012 | Cunningham et al. | |
| 8,287,536 B2 | 10/2012 | Mueller et al. | |
| 8,292,886 B2 | 10/2012 | Kerr et al. | |
| 8,323,310 B2 | 12/2012 | Kingsley | |
| 8,343,150 B2 | 1/2013 | Artale | |
| 8,343,151 B2 | 1/2013 | Siebrecht et al. | |
| 8,357,159 B2 | 1/2013 | Romero | |
| 8,382,792 B2 | 2/2013 | Chojin | |
| 8,388,647 B2 | 3/2013 | Nau, Jr. et al. | |
| 8,398,673 B2 | 3/2013 | Hinchliffe et al. | |
| 8,425,511 B2 | 4/2013 | Olson | |
| 8,430,876 B2 | 4/2013 | Kappus et al. | |
| 8,439,911 B2 | 5/2013 | Mueller | |
| 8,469,957 B2 | 6/2013 | Roy | |
| 8,480,671 B2 | 7/2013 | Mueller | |
| 8,486,107 B2 | 7/2013 | Hinton | |
| 8,512,371 B2 | 8/2013 | Kerr et al. | |
| 8,540,749 B2 | 9/2013 | Garrison et al. | |
| 8,556,929 B2 | 10/2013 | Harper et al. | |
| 8,568,412 B2 | 10/2013 | Brandt et al. | |
| 8,623,017 B2 | 1/2014 | Moses et al. | |
| 8,632,539 B2 | 1/2014 | Twomey et al. | |
| 8,632,564 B2 | 1/2014 | Cunningham | |
| 8,636,761 B2 | 1/2014 | Cunningham et al. | |
| 9,375,227 B2 | 6/2016 | Garrison et al. | |
| 2006/0064085 A1 | 3/2006 | Schechter et al. | |
| 2006/0079890 A1 | 4/2006 | Guerra | |
| 2006/0217697 A1 | 9/2006 | Lau et al. | |
| 2007/0173814 A1 | 7/2007 | Hixson et al. | |
| 2007/0260242 A1 | 11/2007 | Dycus et al. | |
| 2009/0018535 A1 | 1/2009 | Schechter et al. | |
| 2009/0112229 A1 | 4/2009 | Omori et al. | |
| 2009/0131933 A1 | 5/2009 | Ghabrial et al. | |
| 2010/0094271 A1 | 4/2010 | Ward et al. | |
| 2010/0130971 A1 | 5/2010 | Baily | |
| 2010/0179543 A1 | 7/2010 | Johnson et al. | |
| 2010/0249769 A1 | 9/2010 | Nau, Jr. et al. | |
| 2010/0280511 A1 | 11/2010 | Rachlin et al. | |
| 2011/0034918 A1 | 2/2011 | Reschke | |
| 2011/0046623 A1 | 2/2011 | Reschke | |
| 2011/0054468 A1 | 3/2011 | Dycus | |
| 2011/0054471 A1 | 3/2011 | Gerhardt et al. | |
| 2011/0060335 A1 | 3/2011 | Harper et al. | |
| 2011/0071523 A1 | 3/2011 | Dickhans | |
| 2011/0077648 A1 | 3/2011 | Lee et al. | |
| 2011/0118736 A1 | 5/2011 | Harper et al. | |
| 2011/0190765 A1 | 8/2011 | Chojin | |
| 2011/0193608 A1 | 8/2011 | Krapohl | |
| 2011/0218530 A1 | 9/2011 | Reschke | |
| 2011/0230880 A1 | 9/2011 | Chojin et al. | |

FOREIGN PATENT DOCUMENTS

| | | | |
|---|---|---|---|
| DE | 2627679 | A1 | 1/1977 |
| DE | 3423356 | A1 | 1/1986 |
| DE | 3612646 | A1 | 4/1987 |
| DE | 8712328 | U1 | 2/1988 |
| DE | 4303882 | A1 | 8/1994 |
| DE | 4403252 | A1 | 8/1995 |
| DE | 19515914 | C1 | 7/1996 |
| DE | 19506363 | A1 | 8/1996 |
| DE | 29616210 | U1 | 11/1996 |
| DE | 19608716 | C1 | 4/1997 |
| DE | 19751106 | A1 | 5/1998 |
| DE | 19738457 | A1 | 3/1999 |
| DE | 19751108 | A1 | 5/1999 |
| DE | 10045375 | A1 | 4/2002 |
| DE | 20121161 | U1 | 4/2002 |
| DE | 20200700931 | | 10/2007 |
| EP | 1159926 | A2 | 12/2001 |
| EP | 1177771 | A1 | 2/2002 |
| EP | 1777771 | A1 | 4/2007 |
| JP | 61501068 | | 9/1984 |

(56) References Cited

FOREIGN PATENT DOCUMENTS

| JP | 65502328 | 3/1992 |
|---|---|---|
| JP | 55106 | 1/1993 |
| JP | 540112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11070124 | 3/1999 |
| JP | 11244298 | 9/1999 |
| JP | 2000102545 A | 4/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001128990 A | 5/2001 |
| SU | 401367 A1 | 10/1973 |
| WO | 0036986 A1 | 6/2000 |
| WO | 0154604 A1 | 8/2001 |
| WO | 05110264 A3 | 4/2006 |
| WO | 2008045348 A2 | 4/2008 |
| WO | 2008045350 A2 | 4/2008 |
| WO | 2009039179 A1 | 3/2009 |

OTHER PUBLICATIONS

U.S. Appl. No. 12/336,970, filed Dec. 17, 2008, Sremcich et al.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.

(56) References Cited

OTHER PUBLICATIONS

Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
Int'l Search Report Extended—EP 12 16 9753.6 and dated Oct. 2, 2012.
Int'l Search Report EP11168419.7 dated Oct. 11, 2011.
Int'l Search Report EP11168419.7 dated Aug. 8, 2011.
Int'l Search Report EP11168455.1 dated Sep. 26, 2011.
Int'l Search Report EP11168458.5 dated Jul. 21, 2011.
Extended European Search Report dated May 6, 2015 from Application No. EP 14199637.1.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06 024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.

* cited by examiner

APPARATUS FOR PERFORMING AN ELECTROSURGICAL PROCEDURE

CROSS-REFERENCE TO RELATED APPLICATIONS

The present application is a continuation application of U.S. patent application Ser. No. 14/035,423, now U.S. Pat. No. 9,375,227, filed on Sep. 24, 2013, which is a divisional application of U.S. patent application Ser. No. 12/792,330, filed Jun. 2, 2010, now U.S. Pat. No. 8,540,749, the contents of each of which are incorporated by reference herein.

BACKGROUND

Technical Field

The present disclosure relates to an apparatus for performing an electrosurgical procedure. More particularly, the present disclosure relates to an electrosurgical apparatus including an end effector assembly having a pair of jaw members that provide a mechanical advantage at the end effector.

Description of Related Art

Electrosurgical instruments, e.g., electrosurgical forceps (open or closed type), are well known in the medical arts and typically include a housing, a handle assembly, a shaft and an end effector assembly attached to a distal end of the shaft. The end effector includes jaw members configured to manipulate tissue (e.g., grasp and seal tissue). Typically, the electrosurgical forceps utilizes both mechanical clamping action and electrical energy to effect hemostasis by heating the tissue and blood vessels to coagulate, cauterize, seal, cut, desiccate, and/or fulgurate tissue. Typically, one or more driving mechanisms, e.g., a drive assembly including a drive rod, is utilized to cooperate with one or more components operatively associated with the end effector to impart movement to one or both of the jaw members.

In certain instances, to facilitate moving the jaw members from an open position for grasping tissue to a closed position for clamping tissue (or vice versa) such that a consistent, uniform tissue effect (e.g., tissue seal) is achieved, one or more types of suitable devices may be operably associated with the electrosurgical forceps. For example, in some instances, one or more types of springs, e.g., a compression spring, may operably couple to the handle assembly associated with the electrosurgical forceps. In this instance, the spring is typically operatively associated with the drive assembly to facilitate actuation of a movable handle associated with the handle assembly to ensure that a specific closure force between the jaw members is maintained within one or more suitable working ranges.

In certain instances, the shaft may bend or deform during the course of an electrosurgical procedure. For example, under certain circumstances, a clinician may intentionally bend or articulate the shaft to gain desired mechanical advantage at the surgical site. Or, under certain circumstances, the surgical environment may cause unintentional or unwanted bending or flexing of the shaft, such as, for example, in the instance where the shaft is a component of a catheter-based electrosurgical forceps. More particularly, shafts associated with catheter-based electrosurgical forceps are typically designed to function with relatively small jaw members, e.g., jaw members that are configured to pass through openings that are 3 mm or less in diameter. Accordingly, the shaft and operative components associated therewith, e.g., a drive rod, are proportioned appropriately. That is, the shaft and drive rod are relatively small.

As can be appreciated, when the shaft is bent or deformed (either intentionally or unintentionally) the frictional losses associated with drive rod translating through the shaft are transferred to the spring in the housing, which, in turn, may diminish, impede and/or prevent effective transfer of the desired closure force that is needed at the jaw members. Moreover, the frictional losses may also lessen the operative life of the spring, which, in turn, ultimately lessens the operative life of the electrosurgical instrument.

SUMMARY

The present disclosure provides an endoscopic forceps. The endoscopic forceps includes a housing having a shaft that extends therefrom having a longitudinal axis defined therethrough. An end effector assembly operatively connects to a distal end of the shaft and includes a pair of first and second jaw members. One or both of the first and second jaw members is movable relative to the other jaw member from an open position to a clamping position. One of the first and second jaw members includes one or more cam slots defined therein and is configured to receive a cam member that upon movement thereof rotates the jaw members from the clamping position to the open position. A resilient member is operably coupled to one or both of the jaw members. The resilient member is configured to bias the first and second jaw members in the clamping position and provide a closure force on tissue disposed therebetween.

The present disclosure provides an endoscopic forceps. The endoscopic forceps includes a housing having a shaft that extends therefrom having a longitudinal axis defined therethrough. An end effector assembly operatively connects to a distal end of the shaft and includes a pair of first and second jaw members. The first and second jaw members each having a respective detent operably disposed at a proximal end thereof. The first and second jaw members movable relative to one another from a clamping position wherein the first and second jaw members cooperate to grasp tissue therebetween to an open position wherein the first and second jaw members are disposed in spaced relation relative to one another. A cam assembly is movable along the longitudinal axis and includes one or more cam slots defined therein. The one or more cam slots are configured to receive the detent associated with the respective first and second jaw members. A resilient member operably couples to the cam assembly and is configured to bias the first and second jaw members in the clamping position and provide a closure force on tissue disposed therebetween.

The present disclosure provides an endoscopic forceps. The endoscopic forceps includes a housing having a shaft that extends therefrom having a longitudinal axis defined therethrough. An end effector assembly operatively connects to a distal end of the shaft and includes a pair of first and second jaw members. One or both of the first and second jaw members is movable relative to the other jaw member that is stationary from an open position to a clamping position. A support member is operably disposed at a distal end of the shaft adjacent the end effector. A resilient member in mechanical communication with the support member operably couples to the first and second jaw members. The resilient member is configured to bias the first and second jaw members in the clamping position and provide a closure force on tissue disposed therebetween.

In embodiments, a plurality of non-conductive stop members is disposed on an inner facing surface of one or both of the first and second jaw members. The stop members are configured to maintain a uniform distance between the first and second jaw members along the length thereof during tissue sealing.

The present disclosure also provides a method for performing a laparoscopic surgical procedure. The method includes providing an endoscopic instrument that includes an end effector assembly including a pair of first and second jaw members. One or both of the first and second jaw members is movable relative to the other from a clamping position to an open position. The movable jaw member includes one or more cam slots defined therein that is configured to receive a cam member. A resilient member is operably coupled to one or both of the first and second jaw members. The resilient member is configured to bias the first and second jaw members in the clamping position and provide a closure force on tissue disposed therebetween. A step of the method includes biasing the first and second jaw members in the clamping position with the resilient member for positioning the end effector adjacent to tissue. Moving the movable jaw member to the open position is a step of the method. Positioning tissue between the first and second jaw members is another step of the method. And, moving the movable jaw member to the clamping position is still yet another step of the method.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1A:
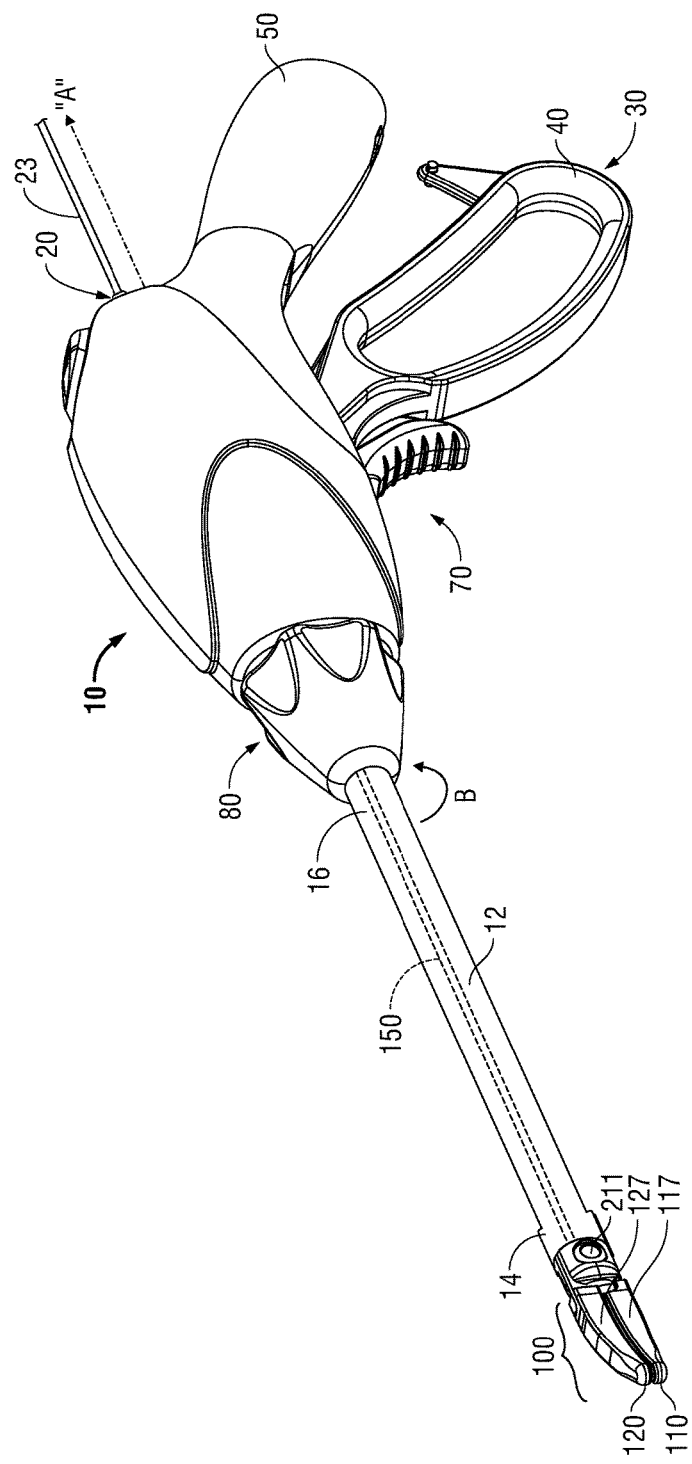
FIG. 1A is a side, perspective view of an endoscopic bipolar forceps showing an end effector assembly including jaw members in a closed configuration according to an embodiment of the present disclosure.
Figure 1B:
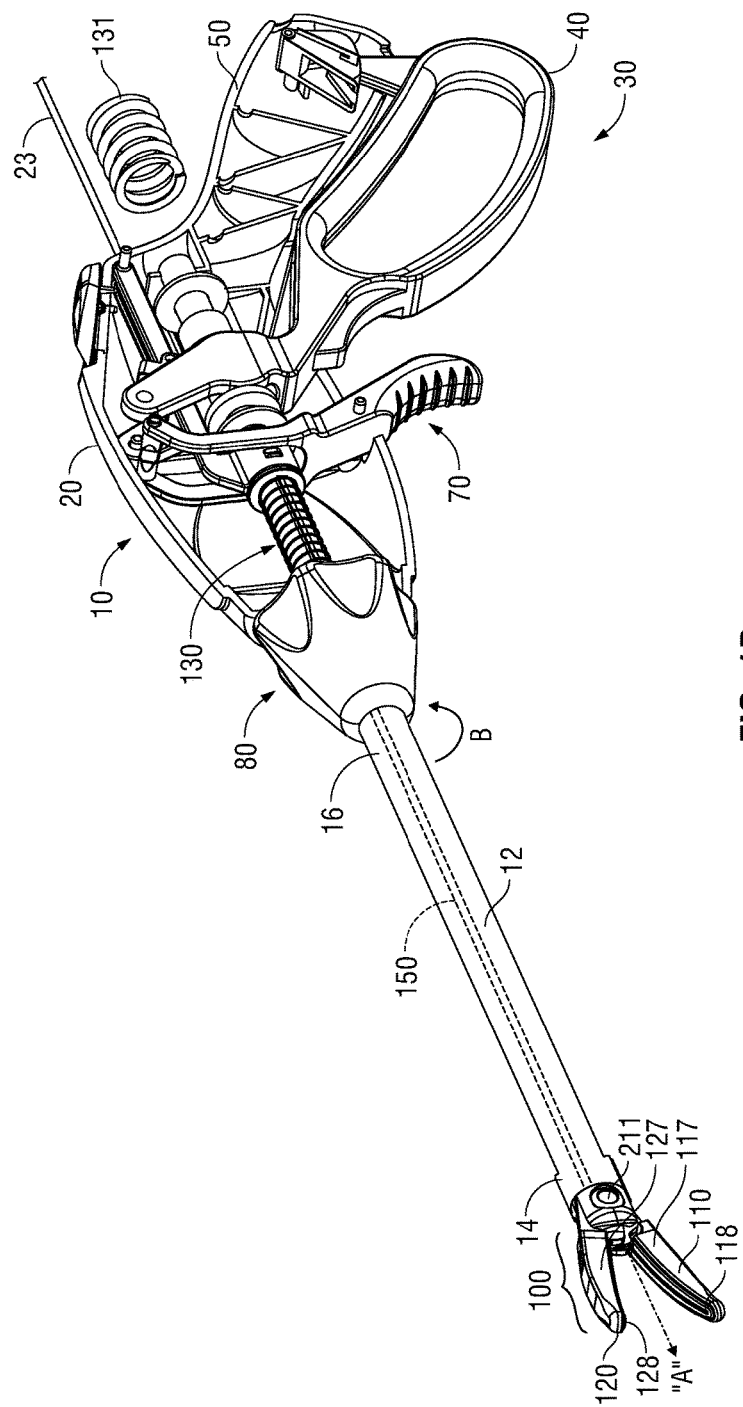
FIG. 1B is a side, perspective view of the endoscopic bipolar forceps depicted in FIG. 1A illustrating internal components of a handle assembly associated with the endoscopic bipolar forceps.

With reference to FIGS. 1A and 1B, an illustrative embodiment of an electrosurgical apparatus, e.g., a bipolar forceps 10 (forceps 10) is shown. Forceps 10 is operatively and selectively coupled to a suitable power source, such as, for example, an electrosurgical generator (not shown) for performing an electrosurgical procedure. As noted above, an electrosurgical procedure may include sealing, cutting, cauterizing coagulating, desiccating, and fulgurating tissue all of which may employ RF energy. The generator may be configured for monopolar and/or bipolar modes of operation. The generator may include or is in operative communication with a system (not shown) that may include one or more processors in operative communication with one or more control modules that are executable on the processor. The control module (not explicitly shown) may be configured to instruct one or more modules to transmit electrosurgical energy, which may be in the form of a wave or signal/pulse, via one or more cables (e.g., a cable 23) to the forceps 10.

Forceps 10 is shown configured for use with various electrosurgical procedures and generally includes a housing 20, electrosurgical cable 23 that connects the forceps 10 to a source of electrosurgical energy (e.g., the electrosurgical generator), a handle assembly 30, a rotating assembly 80, a trigger assembly 70, a drive assembly 130 (see FIG. 1B), and an end effector assembly 100 that operatively connects to a drive element 150 of the drive assembly 130. End effector assembly 100 includes opposing jaw members 110 and 120 (FIGS. 1A and 1B) that mutually cooperate to grasp, seal and, in some cases, divide large tubular vessels and large vascular tissues. The drive assembly 130 is in operative communication with handle assembly 30 for imparting movement of one or both of a pair of jaw members 110, 120 of end effector assembly 100. Conventional drive assemblies typically utilize one or more types of springs, e.g., a compression spring, to facilitate closing the jaw members 110 and 120. For illustrative purposes, a compression spring 131 (see FIG. 1B) is shown separated from the housing 20.

With continued reference to FIGS. 1A and 1B, forceps 10 includes a shaft 12 that has a distal end 14 configured to mechanically engage the end effector assembly 100 and a proximal end 16 that mechanically engages the housing 20. In the drawings and in the descriptions that follow, the term "proximal," as is traditional, will refer to the end of the forceps 10 which is closer to the user, while the term "distal" will refer to the end that is farther from the user.

Handle assembly 30 includes a fixed handle 50 and a movable handle 40. Fixed handle 50 is integrally associated with housing 20 and handle 40 is movable relative to fixed handle 50. Movable handle 40 of handle assembly 30 is ultimately connected to the drive assembly 130, which together mechanically cooperate to impart movement of one or both of the jaw members 110 and 120 to move from a clamping or closed position (FIG. 1A), wherein the jaw members 110 and 120 cooperate to grasp tissue therebetween, to an open position (FIG. 1B), wherein the jaw members 110 and 120 are disposed in spaced relation relative to one another.

Jaw members 110, 120 are operatively and pivotably coupled to each other and located adjacent the distal end 14 of shaft 12. Respective electrically conductive seal plates 118 and 128 are operably supported on and secured to respective jaw housings 117 and 127 of respective the jaw members 110 and 120, described in greater detail below. For the purposes herein, jaw members 110 and 120 include jaw housings 117 and 127 that are configured to support sealing plates 118 and 128, respectively.

For a more detailed description of the forceps 10 including handle assembly 30 including movable handle 40, rotating assembly 80, trigger assembly 70, drive assembly 130, jaw members 110 and 120 (including coupling methods utilized to pivotably couple the jaw members 110 and 120 to each other) and electrosurgical cable 23 (including line-feed configurations and/or connections), reference is made to commonly owned U.S. Pat. No. 7,766,910 filed on Nov. 9, 2006.

Figure 2:
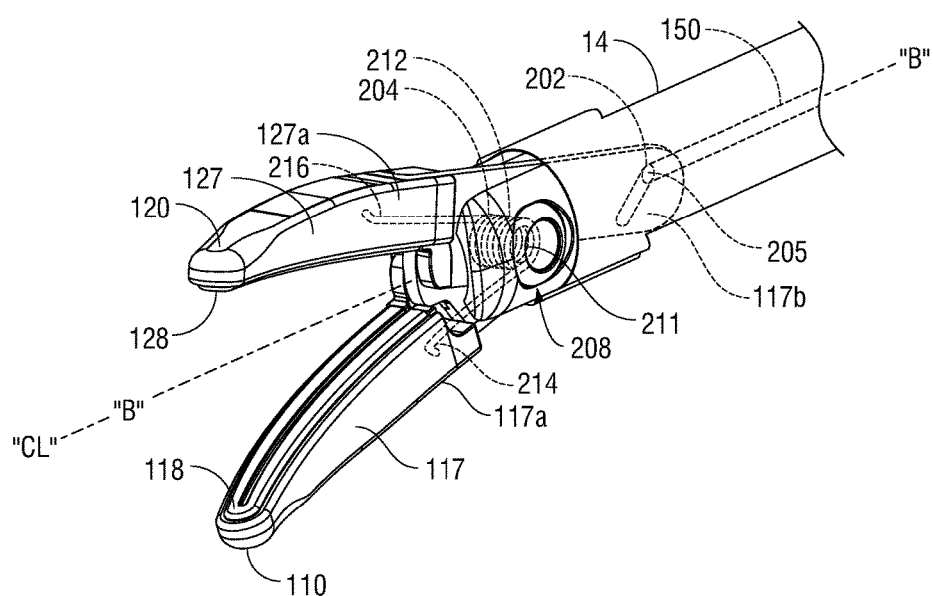
FIG. 2 is a schematic view of the jaw members depicted in FIGS. 1A and 1B operably coupled to a jaw housing associated with each of the jaw members.

Turning now to FIG. 2, one embodiment of jaw housings 117 and 127 is shown. It should be noted that in accordance with the present disclosure one or both of the jaw housings 117 and 127 may include a proximal end that is configured to support one or more cam slots 202 and resilient members 204 to facilitate closing in of the jaw members 110 and 120. Jaw members 110 and 120 are substantially identical to each other, and, in view thereof, and so as not to obscure the present disclosure with redundant information, the operative components associated with the jaw housing 117 are described in further detail with respect to jaw member 110, and only those features distinct to jaw member 120 and jaw housing 127 will be described hereinafter.

With continued reference to FIG. 2, jaw member 110, jaw housing 117, and operative components associated therewith may be formed from any suitable material, including but not limited to metal, metal alloys, plastic, plastic composites, etc. In the embodiment illustrated in FIG. 2, jaw member 110 is formed from metal.

A distal end 117a of the jaw housing 117 of jaw member 110 is configured to securely engage the electrically conductive seal plate 118. A portion of a proximal end 117b of the jaw member 110 is operably secured to the distal end 14 of the shaft 12. More particularly, a portion of proximal end 117b operably couples to the distal end 14 and is in operative communication with the drive element 150 of the drive assembly 130 such that movement of the drive element 150 causes one or both of the jaw members 110 and 120 to move from the closed or clamping position to the open position and vice versa. For example, in one particular embodiment, when the drive element 150 is "pulled," i.e., moved or translated proximally, one or both of the jaw members 110 and 120 is/are caused to move away from the other. Alternatively, and if desired, the drive assembly 130 including the drive element 150 may be configured such that when the drive element 150 is "pushed," i.e., moved or translated distally, one or both of the jaw members 110 and 120 are caused to move away from each other. In certain instances, it may prove useful to have a drive element 150 that is flexible. More particularly, where the drive element 150 is operatively associated with an endoluminal instrument the drive element 150 may be substantially flexible to accommodate bends typically associated with that type of instrument when the bipolar forceps 10 is remotely actuatable relative to the patient.

In the illustrated embodiment, proximal end 117b of the jaw housing 110 includes a generally elongated configuration that may be rectangular, circumferential or combination thereof in shape.

Proximal end 117b of the jaw member 110 includes one or more cam slots 202 defined therein that support one or more cam members 205 (see FIG. 2). More particularly, cam slot 202 is of suitable proportion and configured to receive cam member 205 and is operably formed and/or positioned at the proximal end 117b of the jaw housing 117. Cam slot 202 includes a generally oblique configuration with respect to a longitudinal axis "A-A" that is parallel to a longitudinal axis "A-A" defined through the shaft 12, see FIGS. 1A and 2. Cam slot 202 may extend at an angle that ranges from about 5° to about 30° with respect to the longitudinal axis "B-B." In the embodiment illustrated FIG. 2, cam slot 202 extends at an angle that is approximately equal to 45° with respect to the longitudinal axis "B-B." The angle of the cam slot 202 may be selectively varied depending upon a particular instrument, use or manufacturing preference.

An opening 208 is defined in and extends through the jaw housing 117b and is configured to receive a spring pin 211. Opening 208 is shown engaged with spring pin 211 and as such is not explicitly visible. In the embodiment illustrated in FIG. 2, a portion of the spring pin 211 is dimensioned to securely engage the resilient member 204.

One or more types of resilient members 204 may be operably associated with the housing 117 and includes, for example, a torsion spring that is utilized to generate a closure force on the jaw members 110 and 120 when the jaw members 110 and 120 are in a closed or clamped position. The resilient member 204 cooperates with the drive assembly 130 to provide the necessary closure force on the jaw members 110 and 120 for sealing tissue, e.g., in the range of about 3 kg/cm$^2$ to about 16 kg/cm$^2$.

Resilient member 204 operably engages jaw housings 117 and 127 and is biased in a closed orientation. More particularly, a proximal end 212 of suitable proportion and having a generally circumferential configuration is dimensioned to securely couple to the spring pin 211. Two generally elongated fingers 214 and 216 extend from proximal end 212 adjacent the proximal ends of the jaw members, e.g., proximal end 117b of jaw member 110 and a proximal end (not explicitly shown) of the jaw member 120, and fixedly couple to a respective distal end of the jaw member, e.g., distal end 117a of jaw member 117 and a distal end 127a of the jaw member 120. In the embodiment illustrated in FIG. 2, the resilient member 204 biases the jaw members 110 and 120 toward each other to a closed position such that a consistent uniform seal is effected to tissue. More particularly, the configuration of the resilient member 204 is designed such that each the elongated fingers 214 and 216 are operably disposed adjacent a respective imaginary center-line "CL" that extends through each of the jaw members 110 and 120, see FIG. 2. In this instance, the force from each of the elongated fingers 214 and 216 is evenly distributed to and throughout a respective jaw member.

One or more types of lubricious materials (not shown), e.g., PTFE, may coat cam slot 202 or an inner peripheral surface thereof. Coating the cam slot 202 with the lubricious material facilitates movement of the cam member 205 within the cam slot 202 when the drive element 150 is translated proximally (or distally depending on a particular configuration).

In an assembled configuration each of the jaw members 110 and 120 are positioned in side-by-side relation. Cam member 205 is operably disposed within cam slot 202 associated with jaw member 110 and a corresponding cam slot (not explicitly shown) associated with jaw member 120. Spring pin 211 is positioned within the opening associated with jaw member 110 and a corresponding opening (not explicitly shown) associated with jaw member 120. As noted above, the spring pin 211 provides a point of pivot for each of the jaw members 110 and 120. Once assembled, the jaw members 110 and 120 may be pivotably supported at the distal end 14 of the shaft 12 by known methods, such as, for example, by the method described in commonly-owned U.S. Patent Publication No. 2007/0260242 filed on Jul. 11, 2007.

In use, initially jaw members 110 and 120 are biased in a closed position under the closure and/or sealing force provided by the resilient member 204. Proximal movement of movable handle 40 causes the drive element 150 to move proximally. Proximal movement of the drive element 150 causes cam member 205 positioned within the cam slot 202 to move proximally against the bias of the resilient member 204, which, in turn, causes both of the jaw members 110 and 120 to move relative to one another, such that tissue is positioned between the jaw members 110 and 120. Once tissue is positioned between the jaw members 110 and 120 the movable handle 40 is released, which, in turn, causes the jaw members 110 and 120 to move toward one another under the biasing force of the resilient member 204 which generates a sealing or closure force on the tissue disposed between the jaw members 110 and 120. The resilient member 204 provides an additional mechanical advantage at the jaw members 110 and 120 and reduces the frictional losses that are typically associated with conventional forceps when a drive rod is translated within a shaft to make the necessary closure force to seal tissue, e.g., the closure force is offloaded and/or diminished by the resilient member 204.

Figure 3A:
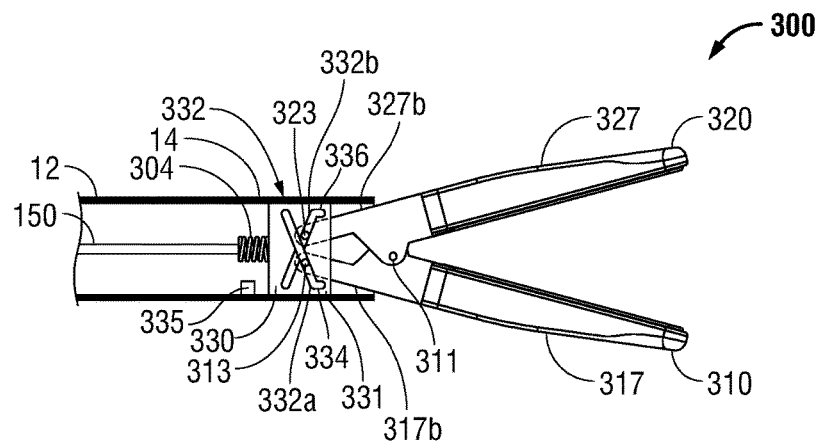
FIGS. 3A and 3B are schematic views of jaw members operably coupled to a distal end of the endoscopic forceps depicted in FIGS. 1A and 1B according to another embodiment of the present disclosure.
Figure 3B:
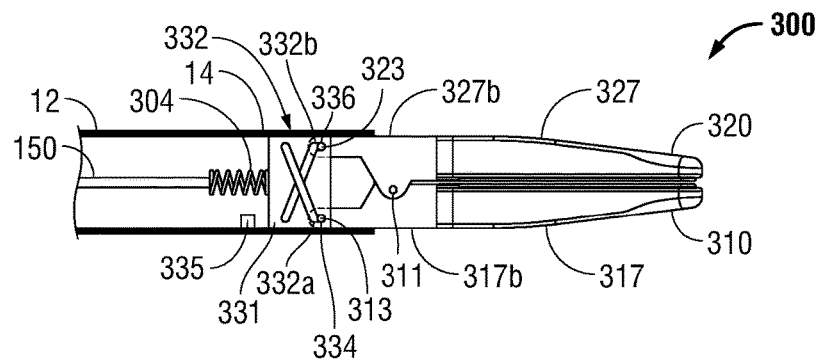

With reference to FIGS. 3A and 3B, another embodiment of an end effector 300 that is configured for use with the forceps 10 is illustrated. End effector 300 is substantially identical to end effector 100, and, in view thereof, and so as not to obscure the present disclosure with redundant information, and only those features distinct to end effector 300 will be described hereinafter.

End effector 300 includes jaw members 310 and 320. As described above with respect to jaw members 110 and 120, jaw members 310 and 320 are pivotably coupled to each other via a spring pin or pivot pin 311. More particularly, pivot pin 311 operably couples the jaw members 310 and 320 about a medial portion of a respective jaw housing 317 and 327 (FIG. 3A). Pivot pin 311 maintains the jaw members 310 and 320 in a substantially fixed position with respect to the longitudinal axis "A-A" when the jaw members 310 and 320 are pivoting or rotating about the pivot pin 311. That is, the jaw members 310 and 320 do not translate along the longitudinal axis "A-A" when movable handle 40 is moved.

A respective detent 313 and 323 is operably disposed at a respective proximal end 317b and 327b of the jaw members 310 and 320, respectively. In the embodiment illustrated in FIGS. 3A and 3B, the detents 313 and 323 are configured to rotate the respective jaw members 310 and 320 from an open position (FIG. 3A) to a closed or clamping position (FIG. 3B) when the movable handle 40 is moved proximally. Detents 313 and 323 are proportioned to movably couple to a cam assembly 330.

Cam assembly 330 translates or moves along the longitudinal axis "A-A" when the movable handle 40 is moved proximally and/or distally. To this end, cam assembly 330 is suitably shaped and proportioned to movably reside within the shaft 12 adjacent the distal end 14. For illustrative purposes, cam assembly 330 is shown elongated with a generally rectangular shape. One or more cam slots 332 are operably disposed on or defined in the cam assembly 330. In the embodiment illustrated in FIGS. 3A and 3B, two intersecting cam slots 332a and 332b are defined in the cam assembly 330. The cam slots 332a and 332b are proportioned to receive a respective detent 313 and 323 such that the detents 313 and 323 are movable along a length of the respective cam slots 332a and 332b.

Each of the cam slots 332a and 332b includes a respective distal end 334 and 336. The distal ends 334 and 336 are configured to function as latches. More particularly, the distal ends 334 and 336 maintain the respective detents 313 and 323 in a substantially fixed position after the movable handle 40 is moved a predetermined distance proximally and the jaw members 310 and 320 are in the clamping position.

One or more suitable unlatching devices or configurations may be utilized to unlatch the detents 313 and 323 from the respective distal ends 334 and 336. For example, and in one particular embodiment, one or more detents 335 may be operably disposed along an internal surface of the shaft 12. In this instance, the detent 335 may be configured to contact a portion, e.g., a bottom surface 331, of the cam assembly 330 when the movable handle 40 is moved through an "unlatching" stroke, see FIGS. 3A and 3B. Accordingly, when movable handle 40 is moved through the "unlatching" stroke, the detent 335 contacts the bottom surface 331 of the cam assembly 330, which, in turn, unlatches the detents 313 and 323 from the respective distal ends 334 and 336. Other latching and unlatching devices and/or configurations may be utilized to latch and unlatch the detents 313 and 323 from the respective distal ends 334 and 336.

One or more types of resilient members 304 operably couple to the drive element 150 and to the cam assembly 330. Resilient member 304 may be any suitable resilient member, e.g., a compression spring. A distal end of the drive element 150 operably couples to a proximal end of the resilient member 304 and proximal end of the cam assembly 330 operably couples to a distal end of the resilient member 304. The resilient member 304 operably couples to the distal end of the drive element 150 and proximal end of the cam assembly 330 via any suitable coupling methods. As described above with resilient member 204, resilient member 304 cooperates with the drive assembly 130 to provide the necessary closure force on the jaw members 310 and 320 for sealing tissue, e.g., in the range of about 3 kg/cm$^2$ to about 16 kg/cm$^2$.

In use, initially jaw members 310 and 320 are biased in an open position (FIG. 3A). Tissue is positioned between the jaw members 310 and 320. Thereafter, the movable handle 40 is moved proximally causing the drive element 150 to move proximally. Proximal movement of the drive element 150 moves the resilient member 304 proximally, which, in turn, moves the cam assembly 330 proximally. Proximal movement of the cam assembly 330 causes the detents 313 and 323 to move within the respective cam slots 332a and 332b and to the respective distal ends 334 and 336 until the detents 313 and 323 are latched into a closed or clamping position (FIG. 3B). In the latched position, the requisite sealing or closure force is present on the tissue disposed between the jaw members 310 and 320. Thereafter, electrosurgical energy is transmitted to seal surfaces 318 and 328 operably associated with respective jaw members 310 and 320 such that a desired tissue effect, e.g., a tissues seal, may be achieved on the tissue disposed between the jaw members 310 and 320. To open the jaw members 310 and 320, the moveable handle 40 is moved through an "unlatching" stroke that unlatches or releases the detents 313 and 323 from the respective distal ends 334 and 336 such that the jaw members 310 and 320 return to the initial open position.

Figure 4A:
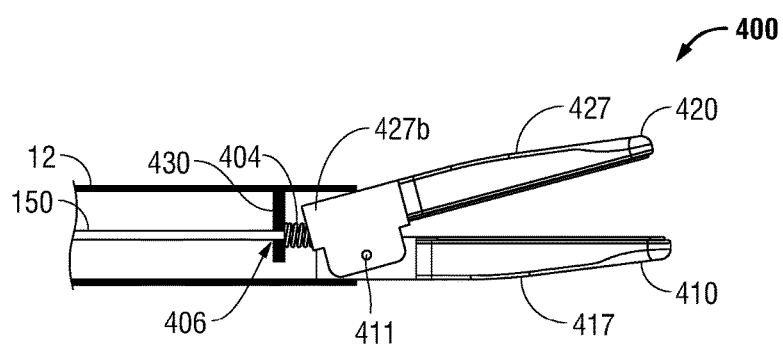
FIGS. 4A and 4B are schematic views of jaw members operably coupled to a distal end of the endoscopic forceps depicted in FIGS. 1A and 1B according to yet another embodiment of the present disclosure.
Figure 4B:
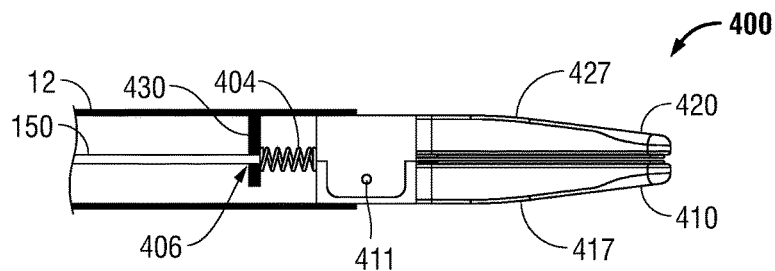

With reference to FIGS. 4A and 4B, an end effector 400 that is configured for use with the forceps 10 is illustrated. End effector 400 is substantially identical to end effectors 100 and 300, and, in view thereof, and so as not to obscure the present disclosure with redundant information, only those features distinct to end effector 400 will be described hereinafter.

End effector 400 includes jaw members 410 and 420. In the embodiment illustrated in FIGS. 4A and 4B, one of the jaw members, e.g., jaw members 420, is movable, and one of the jaw members, e.g., jaw member 410, is stationary. This configuration of jaw members 420 and 410 may be reversed to accommodate various surgical procedures. Jaw members 410 and 420 are pivotably coupled to one another via a pivot pin 411.

A support structure or member 430 is operably disposed along an internal frame of the shaft 12 adjacent the distal end 14. More particularly, the support structure 430 is operably coupled to a top portion of the internal frame of the shaft 12. Support structure 430 is configured to mechanically communicate with a resilient member 404. More particularly, the support structure 430 provides a substantially rigid surface that is configured to compress the resilient member 404 when the resilient member 404 is moved proximally and the movable jaw member 420 is moved to the open position. To this end, support structure 430 may have any suitable shape. In the embodiment illustrated in FIGS. 4A and 4B, support structure 430 includes a generally circumferential configuration having an aperture 406 of suitable proportion defined therethrough. Aperture 406 is includes a diameter that is sized to receive the drive element 150 (or portion thereof) that includes a distal end that operably couples to a proximal end 427b of the movable jaw member 420. More particularly, the diameter of the aperture 406 is such that the drive element 150 is movable through the aperture 406 when the movable handle 40 is moved proximally and/or distally. Additionally, the aperture 406 is proportioned such that the resilient member 404 is prevented from translating therethrough when the movable handle 40 is moved proximally and/or distally.

In the embodiment illustrated in FIGS. 4A and 4B, the support structure 430 is configured to maintain the drive element 150 in a substantially fixed off-set orientation above the pivot pin 411, see FIG. 4A, for example. Having the support structure 430 configured in such a manner facilitates moving the jaw member 420 about the pivot pin 411.

Resilient member 404 is operably disposed between the support structure 430 and the proximal end 427b of the jaw housing 427. In an uncompressed state, resilient member 404 cooperates with the support structure 430 to provide the necessary closure force on the jaw members 410 and 420 for sealing tissue, e.g., in the range of about 3 kg/cm$^2$ to about 16 kg/cm$^2$. To this end, the resilient member 404 may be any suitable resilient spring, e.g., a compression spring 404, including, but not limited to those previously described herein. The compression spring 404 is proportioned such that the drive element 150 is positionable therethrough, FIG. 4A.

In use, initially jaw members 410 and 420 are biased in a closed position under the closure and/or sealing force provided by the compression spring 404 (FIG. 4B). Proximal movement of movable handle 40 causes the drive element 150 to move proximally. Proximal movement of the drive element 150 causes the moveable jaw member, e.g., jaw member 420, to move relative to the stationary jaw member, e.g., jaw member 410, such that tissue is positioned between the jaw members 410 and 420. Once tissue is positioned between the jaw members 410 and 420 the movable handle 40 is released, which, in turn, causes the jaw member 420 to move toward jaw member 410 under the biasing force of the compression spring 404 which generates a sealing or closure force on the tissue disposed between the jaw members 410 and 420. The compression spring 404 provides an additional mechanical advantage at the jaw members 410 and 420 and reduces the frictional losses that are typically associated with conventional forceps when a drive rod is translated within a shaft to make the necessary closure force to seal tissue, e.g., the closure force is offloaded and/or diminished by the compression spring 404.

From the foregoing and with reference to the various figure drawings, those skilled in the art will appreciate that certain modifications can also be made to the present disclosure without departing from the scope of the same. For example, other resilient members, e.g., leaf springs, compressed gas, resilient bladder, spring washers and bellows, may be operably associated with any of the aforementioned configurations of utilized to generate a closure or sealing force at the jaw members. Moreover, the resilient members 204, 304 and 404 may work in combination with one or more springs located with the shaft 12 or housing 20 that are operatively associated with the drive assembly 130 to generate the necessary forces associated with tissue sealing.

Figure 5:
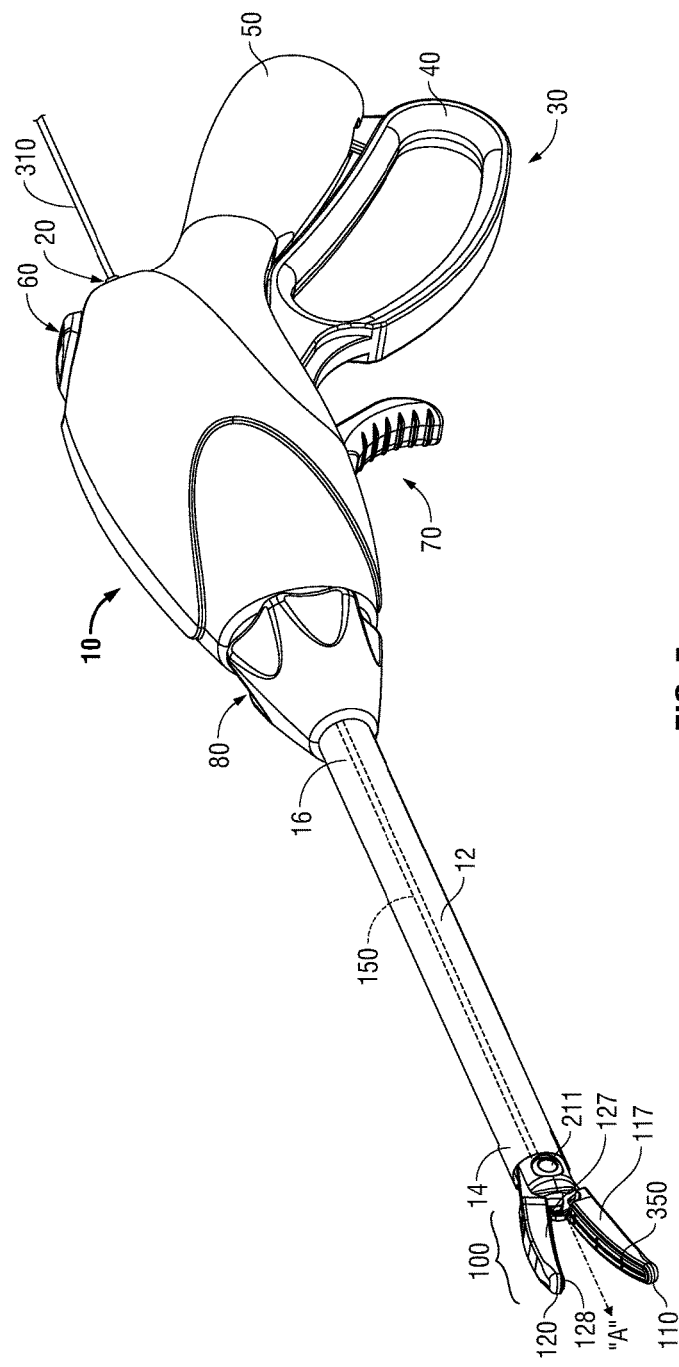
FIG. 5 is a side, perspective view of an endoscopic bipolar forceps showing an end effector assembly including jaw members in an open configuration according to still another embodiment of the present disclosure.

As best seen in FIG. 5, in order to achieve a desired spacing between the electrically conductive surfaces of the respective jaw members, e.g., jaw members 110 and 120, (i.e., gap distance) and apply a desired force to seal the tissue, one or both of the jaw member 110 and/or 120 may include one or more stop members 350 that limit the movement of the two opposing jaw members 110 and 120 relative to one another. The stop member 350 may be disposed on an inner facing surface of one or both of the jaw members 110 and 120. More particularly, stop member 350 extends from a seal surface 118a of seal plate 118 a predetermined distance according to the specific material properties (e.g., compressive strength, thermal expansion, etc.) to yield a consistent and accurate gap distance during sealing. In the illustrated embodiment, the stop members 350 extend from the seal surfaces 118a and 128a a distance that ranges from about 0.001 inches to about 0.006 inches. The gap distance between opposing sealing surfaces 118a and 128a during sealing may range from about 0.001 inches to about 0.006 inches and, preferably, between about 0.002 and about 0.003 inches. The configuration of a seal surface 118a with stop members 350 facilitates in maintaining a uniform distance between the jaw members 110 and 120 along the length thereof during tissue sealing.

For a more detailed description of the stop members 350 and operative components associated therewith, reference is made to commonly-owned U.S. Pat. No. 8,241,284.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An endoscopic forceps, comprising:
   a shaft having a proximal end and a distal end and defining a longitudinal axis;
   an end effector assembly operably coupled to the distal end of the shaft and including a first jaw member and a second jaw member, at least one of the first or second jaw members movable relative to the other jaw member between a clamping position wherein the first and second jaw members cooperate to grasp tissue therebetween and an open position wherein the first and second jaw members are disposed in spaced relation relative to one another;
   a drive rod operably coupled to at least one of the first and second jaw members and configured to translate along the longitudinal axis;
   a support structure disposed along an internal frame of the shaft, wherein the support structure includes an aperture defined therethrough and wherein the drive rod extends through the aperture; and a resilient member disposed between the support structure and a proximal end of at least one of the first or second jaw members.

2. The endoscopic forceps of claim 1, wherein longitudinal translation of the drive rod moves the first and second jaw members between the clamping position and the open position.

3. The endoscopic forceps of claim 1, wherein the support structure provides a rigid surface configured to compress the resilient member when the first and second jaw members are moved between the clamping position and the open position.

4. The endoscopic forceps of claim 1, wherein the resilient member is a compression spring or a leaf spring.

5. The endoscopic forceps of claim 1, further comprising a housing having a moveable handle configured to translate the drive rod along the longitudinal axis.

6. The endoscopic forceps of claim 1, wherein the resilient member provides a closure force between the first jaw member and the second jaw member in the range of about 3 kg/cm$^2$ to about 16 kg/cm$^2$.

7. The endoscopic forceps of claim 1, further comprising a plurality of non-conductive stop members disposed on an inner facing surface of at least one of the first or second jaw members, the non-conductive stop members configured to maintain a uniform distance between the first and second jaw members along a length thereof when in the clamping position.

8. The endoscopic forceps of claim 7, wherein the plurality of non-conductive stop members extend from the inner facing surface a distance that ranges from about 0.001 inches to about 0.006 inches.

9. The endoscopic forceps of claim 1, wherein the resilient member is disposed around at least a portion of the drive rod.

10. The endoscopic forceps of claim 1, wherein the first jaw member is pivotable relative to the second jaw member about a pivot pin.

11. The endoscopic forceps of claim 10, wherein the support structure is configured to maintain the drive rod in a fixed, off-set orientation with respect to the pivot pin.

12. An electrosurgical system, comprising:
an electrosurgical generator; and
an endoscopic forceps configured to couple with the electrosurgical generator, the endoscopic forceps comprising:
a shaft having a proximal end and a distal end and defining a longitudinal axis;
an end effector assembly operably coupled to the distal end of the shaft and including a first jaw member and a second jaw member, at least one of the first or second jaw members movable relative to the other jaw member between a clamping position wherein the first and second jaw members cooperate to grasp tissue therebetween and an open position wherein the first and second jaw members are disposed in spaced relation relative to one another;
a drive rod operably coupled to at least one of the first and second jaw members and configured to translate along the longitudinal axis;
a support structure disposed along an internal frame of the shaft, wherein the support structure includes an aperture defined therethrough and wherein the drive rod extends through the aperture; and
a resilient member disposed between the support structure and a proximal end of at least one of the first or second jaw members.

13. The electrosurgical system of claim 12, wherein longitudinal translation of the drive rod moves the first and second jaw members between the clamping position and the open position.

14. The electrosurgical system of claim 12, wherein the support structure provides a rigid surface configured to compress the resilient member when the first and second jaw members are moved between the clamping position and the open position.

15. The electrosurgical system of claim 12, wherein the resilient member is a compression spring or a leaf spring.

16. The electrosurgical system of claim 12, wherein the endoscopic forceps further comprises a housing having a moveable handle configured to translate the drive rod along the longitudinal axis.

17. The electrosurgical system of claim 12, wherein the resilient member provides a closure force between the first jaw member and the second jaw member in the range of about 3 kg/cm$^2$ to about 16 kg/cm$^2$.

18. The electrosurgical system of claim 12, wherein the endoscopic forceps further comprises a plurality of non-conductive stop members disposed on an inner facing surface of at least one of the first or second jaw members, the non-conductive stop members configured to maintain a uniform distance between the first and second jaw members along a length thereof when in the clamping position.

19. The electrosurgical system of claim 12, wherein the resilient member is disposed around at least a portion of the drive rod.

* * * * *